United States Patent [19]

Burstein et al.

[11] Patent Number: 4,845,769
[45] Date of Patent: Jul. 4, 1989

[54] ANNULAR X-RAY INSPECTION SYSTEM

[75] Inventors: Paul Burstein, Winchester; Allen Krieger, Lexington, both of Mass.

[73] Assignee: American Science and Engineering, Inc., Cambridge, Mass.

[21] Appl. No.: 819,655

[22] Filed: Jan. 17, 1986

[51] Int. Cl.$^4$ .......................... G03B 35/00; G01T 1/20
[52] U.S. Cl. ...................................... 378/58; 250/366; 250/367; 250/368
[58] Field of Search ................. 378/58, 57, 53, 62, 378/99; 250/360.1, 358.1, 359.1, 370 I, 370 G, 367, 368, 366; 340/707, 727

[56] References Cited

U.S. PATENT DOCUMENTS

| | | | |
|---|---|---|---|
| 3,225,193 | 12/1965 | Hilton et al. | 250/71.5 |
| 3,766,387 | 10/1973 | Heffan et al. | 378/146 |
| 4,092,537 | 5/1978 | Stewart | 378/58 |
| 4,303,860 | 12/1981 | Bjorkholm et al. | 250/366 |
| 4,415,928 | 11/1983 | Strolle et al. | 340/727 |
| 4,580,054 | 4/1986 | Shimoni | 250/363 |

FOREIGN PATENT DOCUMENTS

| | | | |
|---|---|---|---|
| 2552887 | 4/1985 | France | 250/368 |
| 57-76466 | 5/1982 | Japan | 250/368 |
| 0207084 | 10/1985 | Japan | 250/368 |
| 31528574 | 10/1978 | United Kingdom | |

Primary Examiner—Carolyn E. Fields
Assistant Examiner—Joseph A. Hynds
Attorney, Agent, or Firm—Pollock, Vande Sande & Priddy

[57] ABSTRACT

A high energy imaging system provides a "slotted" or "slot-shaped" or "rectangular cross-section" beam of illumination to intercept an annular region of an object of revolution as it is rotated. A detector array is located to intercept the illumination beam emanating from the object. The detector array includes an opto-electric transducer imaging a plurality of scintillating optical fiber or fiber bundles. The optical fiber or fiber bundles are located substantially parallel to each other with longitudinal axes substantially perpendicular to the direction of the illuminating radiation and parallel to the longitudinal axis of the object being imaged.

13 Claims, 8 Drawing Sheets

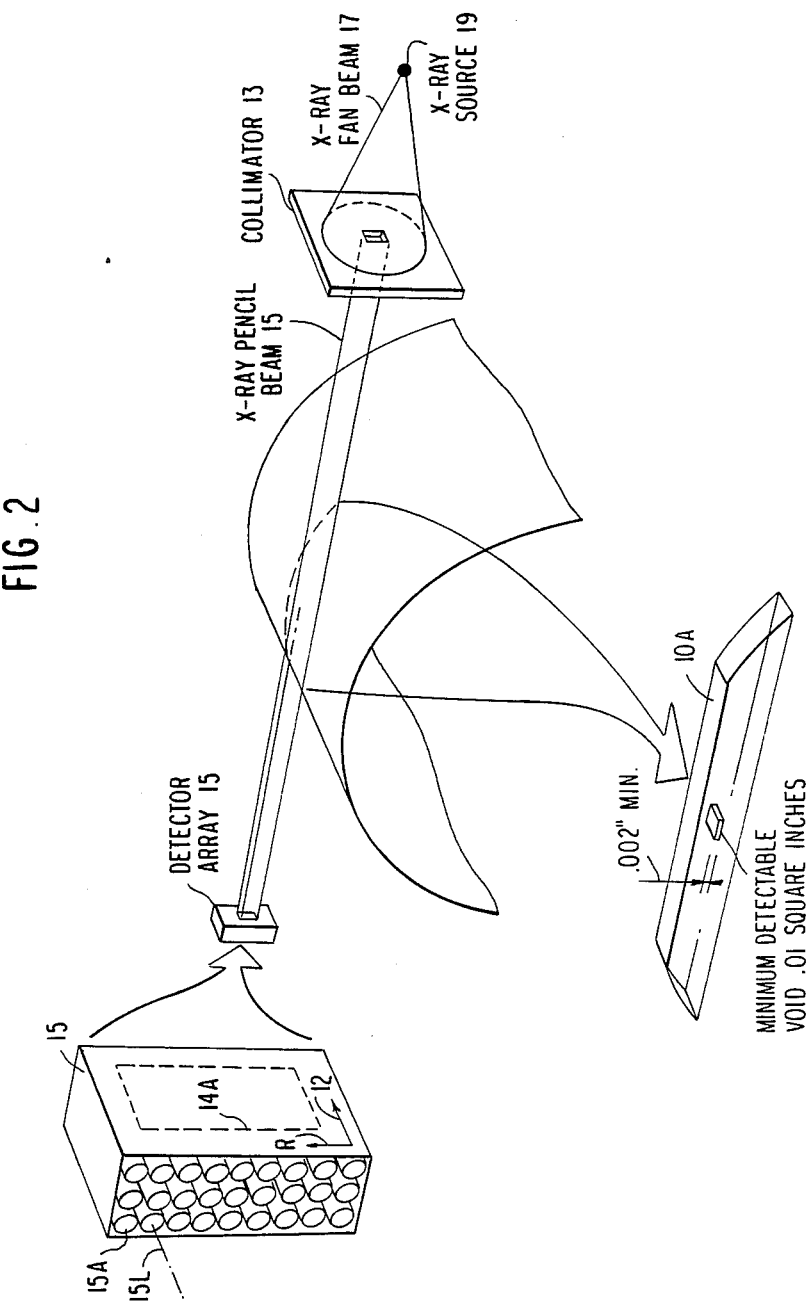

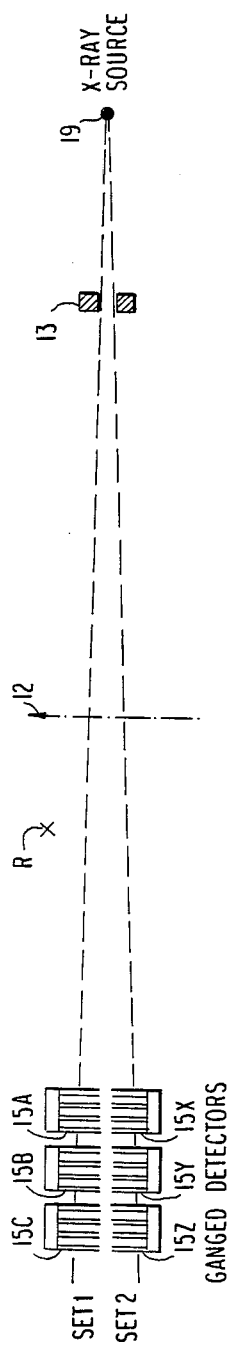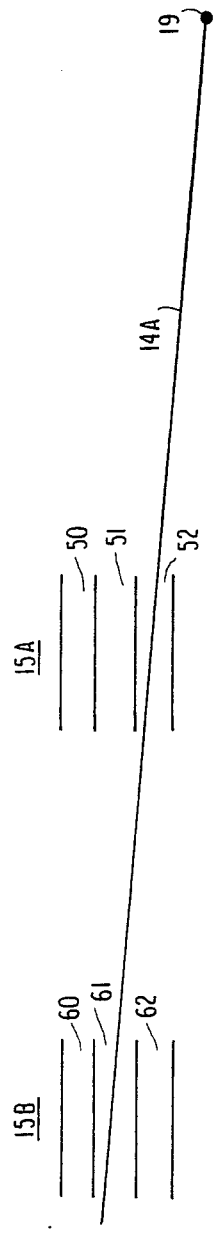

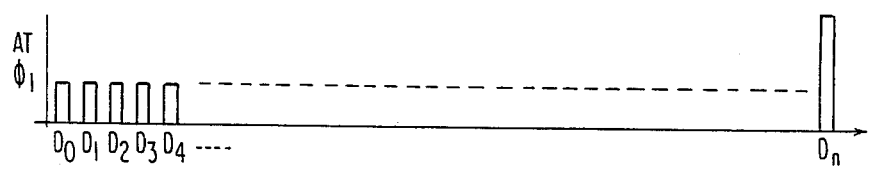
FIG. 8
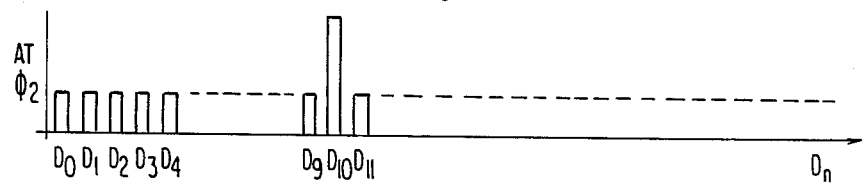
FIG. 9
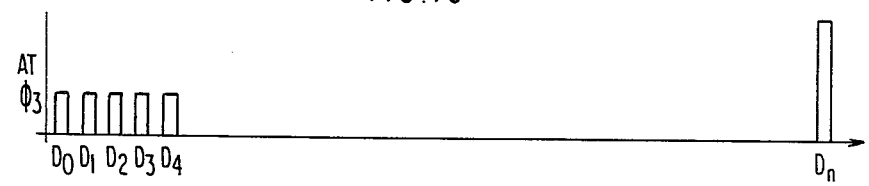
FIG. 10
FIG. 12
| ROTATION ANGLE | DETECTOR ELEMENT | | | | | |
|---|---|---|---|---|---|---|
| | $D_0$ | $D_1$ | $D_2$ | $D_3$ | $D_4$ | $D_5$ |
| $\phi_0$ | $W_{00}$ | $W_{01}$ | $W_{02}$ | $W_{03}$ | $W_{04}$ | $W_{05}$ |
| $\phi_1$ | $W_{10}$ | $W_{11}$ | $W_{12}$ | $W_{13}$ | $W_{14}$ | $W_{15}$ |
| $\phi_2$ | $W_{20}$ | $W_{21}$ | $W_{22}$ | $W_{23}$ | $W_{24}$ | $W_{25}$ |
| $\phi_3$ | $W_{30}$ | $W_{31}$ | $W_{32}$ | $W_{33}$ | $W_{34}$ | $W_{35}$ |
| $\phi_4$ | $W_{40}$ | $W_{41}$ | $W_{42}$ | $W_{43}$ | $W_{44}$ | $W_{45}$ |
| $\phi_5$ | $W_{50}$ | $W_{51}$ | $W_{52}$ | $W_{53}$ | $W_{54}$ | $W_{55}$ |

ANNULAR X-RAY INSPECTION SYSTEM

DESCRIPTION

1. Technical Field

The invention relates to imaging systems, and more particularly imaging systems capable of high resolution in spite of high levels (relative to medical imaging, for example) of illuminating radiation. The invention provides for an imaging system in which spatial resolution may be anisotropic. The invention also provides an imaging system in which the data is recorded to provide for simple visual or machine-based analysis.

2. Background Art

Tangential inspection or imaging of bodies of revolution is well known to those skilled in the arts of high energy imaging, see for example Heffan et al U.S. Pat. No. 3,766,387. In the case of tangential illumination (such as shown in Heffan et al) as is the case with high energy imaging in general, the goal is to produce adequate resolution for whatever purpose the image is being created. As the device being imaged becomes more and more dense, the energy required to illuminate it increases. This is a complicating factor in x-ray imaging, since with increasing energies, the efficiency of the detector also becomes a factor. While it is relatively simple to merely "thicken" a detector to increase its efficiency, this approach normally leads to loss of resolution and hence has strict practical limitations.

Among the materials employed for x-ray detection, in particular, are scintillators, devices which respond to x-rays and generate visible photons. The visible photons can be detected using relatively conventional photo detection devices.

Bjorkholm et al U.S. Pat. No. 4,303,860 provides for minimizing loss of resolution, without compromising x-ray stopping power (or detection efficiency) by providing a scintillator crystal which is "thick" in the direction of the beam (hereinafter "the direction of the beam" refers to the direction in which the beam travels from source to detector), but is "thin" perpendicular thereto. The dimension of the scintillator crystal, in the direction of the beam, can be adjusted at will to increase detection efficiency (stopping power). By shrinking the dimension of the scintillator crystal perpendicular to the direction of the beam, resolution is maintained by limiting the spread of optical photons, before they reach the opto-electronic transducer (photo responsive device). Bjorkholm also mentions that, rather than using a scintillating crystal, scintillating optical fibers can also be used (see FIG. 4). Hilton et al U.S. Pat. No. 3,225,193 also describes scintillating optical fibers. The scintillating optical fiber has the same property as the scintillator crystal, with one additional feature. Because of the properties of a fiber, an optical photon, once generated in a fiber, is confined to that fiber and thus the spread of optical photons is limited by the diameter of the fiber. While the approach described in Bjorkholm et al has significant advantages over the prior art, there are limits to its application. When the beam is thick (in a direction perpendicular to the beam direction) there may be a loss of resolution merely due to beam divergence (since in the main the beam emanates from a point source). This can be overcome by "aiming" each of the fibers at the source. However, this individual fiber alignment makes the detector assembly relatively expensive and should be avoided if possible. Individual fiber alignment also limits the use of the detector to a very narrow range of source/detector distances. Of course this problem can be wholly avoided by limiting the extent of the detector assembly in the direction perpendicular to the beam path, but then this fixes the resolution in that direction, and it is a goal of the invention to ensure that the resolution in any direction can be relatively freely selected.

SUMMARY OF THE INVENTION

The invention overcomes these and other problems in the prior art in providing for tangential illumination of a body of revolution for the purpose of imaging. In accordance with the invention, and in order to provide for relatively fine resolution in one direction with independently selectable resolution in an orthogonal direction, a beam of illumination (preferably x-rays, and of slot, slotted or rectangular cross-section) is directed to tangentially intercept the object to be imaged. The object to be imaged is rotated relative to the source/detector about an axis perpendicular to the direction of the illumination. The detector array is arranged to be intercepted by the illuminating beam, located so that the object being imaged is between the detector array and the source of illumination. A detector array provides for the scintillation function via a plurality of scintillating optical fibers, each with a longitudinal axis arranged parallel to the axis of rotation and perpendicular to the direction of the illumination beam. Because the scintillating optical fibers are arranged generally parallel to the rotational axis of the object, resolution in this direction is controlled in part by the extent of the illuminating beam parallel to the axis, and in part by the length (along the longitudinal axis) of the optical fibers. So long as the extent of the illuminating beam parallel to the fiber axis is less than the length of the optical fibers, resolution is determined by the extent of the illuminating beam. Resolution in this direction can be intentionally degraded up to the limit of the length of the optical fibers. For the purpose of generating electrical signals to represent the photons generated in the scintillating optical fibers, a one-dimensional opto-electric transducer is provided which is arranged to image one end of the scintillating optical fibers. For maximizing resolution in the other direction (that is, along a radius of the object perpendicular to the direction of the illuminating beam), the opto-electric transducer is arranged to lie in a plane which is normal to the axis of the optical fibers. In this plane, the opto-electric transducer can comprise a series of parallel, rectangular, elements. Each of these elements has its long dimension generally parallel to the direction of the beam illumination, and its short dimension in the other direction. The ratio of the long and short dimensions, the aspect ratio, can be increased so as to provide for relatively large detection efficiency (2-10%) while maintaining resolution. A plurality of detector arrays (where each detector array comprises plural scintillating optical fibers and an associated opto-electric transducer) can be serially ganged (arranged one behind the other in the direction of the illumination beam). By projecting the image of a point from one detector array to the next, we can increase detection efficiency without degrading resolution, a pair of arrays can give us about double the detection efficiency of a single array, three arrays approximately three times, and so forth.

The time required to image an object depends on the dwell time which is required to develop signals representative of the x-ray illumination emitted from the object, how much of the object can be simultaneously imaged, and resolution parallel to the axis of rotation. We can substantially decrease the imaging time, without degrading this resolution, by arranging the dimension of the illumination beam parallel to the axis of rotation of the object so as to cover more than twice the desired resolution. Then instead of using a single detector array, or serially ganged detector arrays, we can use opposed detector arrays (whether or not ganged) and actually simultaneously illuminate two adjacent swaths.

In a preferred embodiment of the invention, the source/detector are fixed, and the object being imaged is rotated about a rotation axis. In such an arrangement there are distinctly different spatial resolution requirements, the required resolution in the radial direction (perpendicular to the axis of rotation) is high, whereas the spatial resolution along the rotational axis can be relaxed.

In the preferred embodiment of the invention we provide for imaging of a large rocket motor casing in 8 hours or less. The casing is 83 inches in diameter and 24 feet in length. This detection provides for detecting unbonds (between the chamber and insulator at least 0.002" in the radial dimension) detection of major inclusions or defects, detection of minor defects (0.020"×0.020"×0.005" void, 2% porosity over a cube 0.25" per side), determination of radial dimensions of chamber and insulator to a tolerance of 0.002". These specifications require high resolution in the radial direction, and more relaxed resolution in the axial direction (along the axis of rotation). If axial resolution is reduced to 1", the inspection time could be halved to 4 hours. In this embodiment of the invention the optoelectric transducer has an aspect ratio of 100, its dimensions are 0.001" in the radial direction and 0.100" in the direction of the illumination beam.

Accordingly, the invention provides a high resolution imaging device where resolution is not degraded by high energy illumination and comprises:

a source of high energy illuminating radiation adapted to be directed at an object to be imaged, detector means for developing electrical signals representative of portions of said object illuminated by said high energy illuminating radiation, said detector means comprising:

plural scintillating optical fibers, each with a longitudinal axis, each said plural scintillating optical fibers located to intercept said illuminating radiation with said longitudinal axis substantially perpendicular to a path of said illuminating radiation, and an opto-electric transducer arranged to image one end of said plural scintillating optical fibers.

In accordance with another aspect of the invention, the opto-electronic transducer comprises a plurality of elements, each element developing an electrical signal related to the number of optical photons intercepted by the element of the opto-electronic transducer. In turn, the number of optical photons intercepting a particular opto-electronic transducer element depends upon the quantity of x-ray photons intercepting one of the associated scintillating optical fibers. Of course the quantity of x-ray photons intercepting any particular scintillating optical fiber depends upon the attenuation imposed on the path travelled by the impinging x-ray photons emitted by the source. Thus at any instant of time the set of signals produced by an opto-electronic transducer depends upon a projection, on a plane lying parallel to the longitudinal axis of the optical fibers and perpendicular to beam direction, of the x-ray attenuation presented by the object being imaged. Any anomalies in the x-ray attenuation of the object being imaged will produce corresponding anomalies in the electrical signals produced by the associated opto-electronic transducer. Periodically, the signals produced by the opto-electric transducer are digitized and stored. For a 360° revolution of the object being imaged, the stored signals represent a developed representation of a projection of the x-ray attenuation. Of course as the object is being rotated, it is also being translated (in the axial direction) and thus the sequence of stored signals represent a sequence of developed representations of the projected x-ray attenuation. To the extent that the object being imaged (or the portion of the object being imaged) is uniform or homogenous, the stored electrical signals will be correspondingly uniform or homogenous. Two significant advantages can be readily identified.

If (as is the case) the illuminating beam is arranged so as to extend at least slightly beyond the outer surface of the object being imaged, then the stored signals will readily represent the location of the object's surface, as it is rotated. This representation can be seen in that, at the surface of the object, a large discontinuity exists in x-ray attenuation, for below the object's surface, the x-rays are attenuated by the object whereas just outside the object, x-ray attenuation is significantly less. This discontinuity in the stored representations allows ready accurate measurement of the radius of the object and any dimensional variations in the radius.

Any lack of uniformity or discontinuity in the portion of the object being imaged will of course be represented by a similar lack of uniformity or discontinuity in the stored signals or representations thereof. Because the signals bear a uniform correspondence to different regions in the object, and because the object's motion relative to the source/detector is orderly, the representations of any such discontinuity or non-uniformity will likewise follow an orderly progression. This orderly behavior of representations of discontinuities or non-uniformities provides a significant advantage in data analysis.

For example, if the stored data is merely scanned on a CRT (where there may be a constant of proportionality between the amplitude of the CRT electron beam and the amplitude of the stored data) any discontinuities or non-uniformities can be clearly identified because indications representing the non-uniformities will take on the shape of a smooth and continuous geometric figure. That figure will be a straight line for non-uniformities or discontinuities which are physically circular about the axis of rotation or a smooth curve for point-like discontinuities or non-uniformities. The shape and location of the indications represent the position of the non-uniformity. Clearly the same type of display can be produced in hard copy format. Not only can the existence of these anomalies be identified, but the data will uniquely locate the position of the anomaly in the object being imaged.

Visual display of this information is not essential, although helpful as has been described. Alternatively (or in addition), the existence and location of any anomalies can be deduced based on an algorithm. In other words, the raw data can be analyzed by machine to produce a report identifying size, location and shape of any anomalies in the body being imaged. This is of significant importance in reducing the analysis task imposed on an equipment operator.

Accordingly, the invention provides an imaging system including:

a source of penetrating radiation emitting radiation generally in a first direction, first means for supporting, rotating about a rotational axis, and indexing along said rotational axis, an object to be imaged, said first means located relative to said source so that said penetrating radiation intercepts at least some portion of said object, radiation detecting means including a plurality of scintillating optical fibers, each with a longitudinal axis generally parallel to longitudinal axes of others of said plurality of scintillating optical fibers and to said rotational axis, said radiation detecting means located so that radiation transmitted by said object intercepts said scintillating optical fibers, an opto-electric transducer located generally normal to longitudinal axes of said scintillating optical fibers, said transducer including a plurality of opto-electric transducer elements located adjacent one another and spaced in the direction generally perpendicular to said first direction, and storage means responsive to a time sequence of signals produced by said opto-electric transducer elements for storing representations of said signals in a corresponding sequence.

This aspect of the invention also contemplates the use of a display means responsive to the storage means for producing a visual representation of said signals in a matrix format whereby anomalies in said object are represented in said visual representation by indications whose position in said visual representation are related to the location in the object of the corresponding anomaly. In accordance with this aspect of the invention, the matrix format of the visual representation has an extent in one dimension corresponding to the time required for a complete revolution of the object.

BRIEF DESCRIPTION OF THE DRAWINGS

The present invention will now be further described in the following portions of this specification when taken in conjunction with the attached drawings in which like reference characters identify identical apparatus and in which:

FIG. 2 is an illustration similar to FIG. 1 except that portions of the object are broken away and includes details of the illuminated region and a detail of the detector array;

FIG. 6A is similar to FIG. 4 except that it illustrates serially ganged detectors and opposing detectors;

FIG. 6B is useful in explaining summation of detector element responses to increase efficiency without degrading resolution;

FIGS. 7-11 illustrate how detector element responses can be used to locate anomalies; and particularly FIG. 7 is useful in illustrating the response of a detector array to a particular anomaly as it changes position because of rotation; FIGS. 8-10 illustrate the detector response for different locations of an anomaly; and FIG. 11 illustrates how an anomaly can be located by correlating detector responses to object azimuth, FIG. 12 illustrates a typical matrix storing data from a single rotation of the object.

DETAILED DESCRIPTION OF PREFERRED EMBODIMENTS

Figure 1:
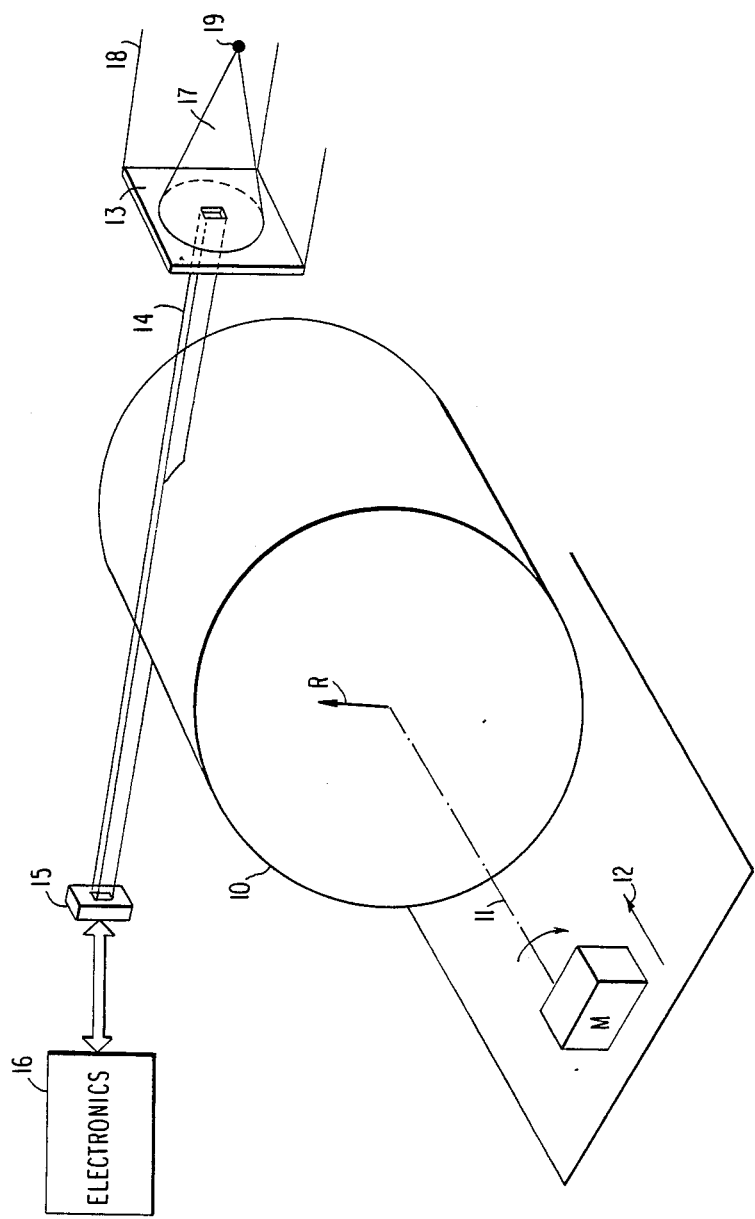
FIG. 1 schematically illustrates the apparatus of the invention.

FIG. 1 is a schematic illustration of the inventive imaging system. As shown in FIG. 1, an object 10 which is to be imaged, is rotated about its longitudinal axis 11, as it is slowly translated (in the direction 12) by a motor M. An illumination source 18 includes an x-ray point source 19 emitting a cone 17 of x-ray beams which impinge on a collimator 13 having a slit. The foregoing apparatus provides for a "slotted" or "slot-shaped" or rectangular cross-section beam 14 which is arranged to tangentially image (intercept) an outer annular portion of the object 10. Although the beam emanates from the point source 19, the radiation is emitted generally in the direction between source 19 and the detector 15. In the following description we will refer to the axial direction as the direction 12, and the direction shown by the arrow R (mutually perpendicular to the axial direction 12 and to the direction of the beam 14) as the radial direction. At least one detector array 15 is arranged so as to intercept the beam 14 emanating from the object 10. The detector array 15 is coupled to appropriate electronics 16 for storage and interpretation of the resulting electrical signals. Electronics 16 may include analog circuitry for filtering and A/D conversion, a computer with suitable mass storage (RAM, disc drive, etc.) for storing representations of the signals produced by the detector array 15 and appropriate output devices (CRT, printer) for data analysis.

In order to develop electrical signals representative of the annular portion of the object 10 which is imaged, the object 10 is slowly rotated about its axis 11, and is indexed along the direction 12. As is known to those skilled in the art, the indexing can be discrete (one step per 360° of rotation) or continuous (moving the width of the beam for each 360° of rotation). As is apparent to those skilled in the art, the illumination emanating from the object 10, and detected at the detector array 15 represents, at any instant of time, the transmissivity of the object 10. The object of the imaging is to detect anomalous changes in the transmissivity of the object indicating cracks, unbonds, flaws, etc. The beam 14 is arranged to be sufficiently extensive (in the radial direction R) so that in addition to illuminating the annular portion of the object 10 which it is desired to inspect, the beam also extends beyond the surface of the object 10. This enables detection of the tolerance within which the radius of the outer edge of the object 10 approaches its design goal. The invention is particularly directed at the detector array 15, and its orientation relative to the other elements of the imaging system. Reference is now made to FIG. 2 for a more detailed showing of the elements of the detector array 15 in relation to the apparatus shown in FIG. 1.

FIG. 2 shows many of the same elements as is shown in FIG. 1, except that the object 10 is shown in schematic fashion, and the portion of the object 10 illuminated at any instant in time (object segment 10A) is shown in detail, along with a more detailed schematic representation of the detector array 15.

Referring first to the blown up portion of FIG. 2 showing the illuminated segment 10A of the object 10, those skilled in the art will understand that the intensity and distribution of x-rays emanating from the object 10 is determined by, and represent, the accumulated effects of the integral along the beam of the density distribution in the portion 10A. As will become apparent, the detector array 15 is arranged so that the resolution in the radial direction is the 0.002" shown in FIG. 2. Referring now to the left portion of FIG. 2, the detector array 15 is shown schematically, enlarged. Outline 14A shows the footprint of the x-ray energy emanating from the object 10. The detector array 15 includes a plurality of scintillating optical fibers or scintillating optical fiber bundles 15A. These plural optical fibers (below we refer to optical fibers, although those skilled in the art will understand that the term optical fiber includes an optical fiber bundle) are arranged with a longitudinal axis 15L, parallel to each other and parallel (or substantially parallel) to the axial direction 12. Individual x-ray photons are detected when they interact in one of the scintillating optical fibers to produce a plurality of optical photons. It should be apparent that the stopping power or detection efficiency of the detector array 15, depends on the dimension of the array parallel to the direction of the beam 14, the larger this dimension, the greater the stopping power or detection efficiency. Not shown in FIG. 2 is an opto-electric transducer. However, the transducer is arranged to image one end of the optical fibers 15A (specifically the end of the optical fibers 15A not illustrated in FIG. 2) and so the transducer is located normal to the axes 15L. Accordingly, the opto-electric transducer can be considered to lie in the plane which is generally parallel to the direction of the beam 14 and perpendicular to the axis 15L of the optical fibers.

Figure 3:
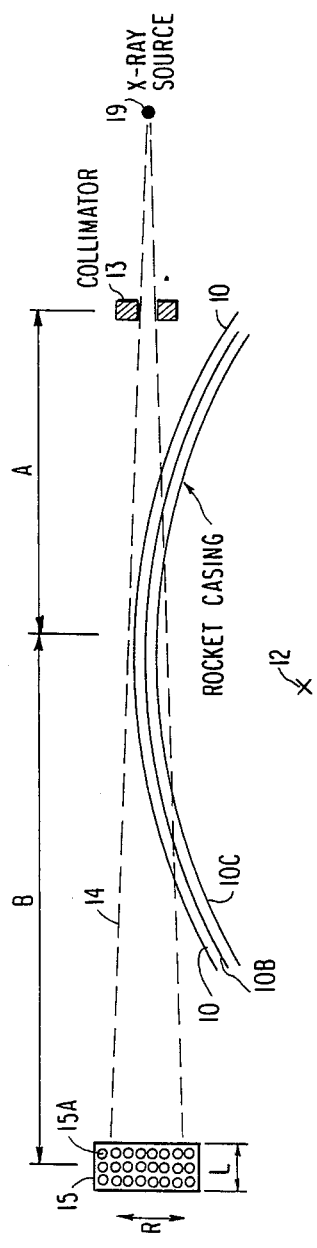
FIGS. 3 and 4 are axial and orthogonal sections of FIG. 1, respectively, showing orientation of the detector array relative to the illumination beam.
Figure 4:
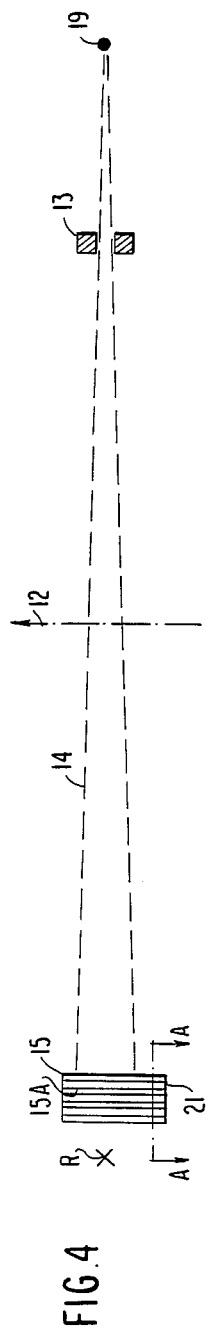

FIGS. 3 and 4 are a cross-section of FIG. 1 to show in more detail the relationships already referred to. Referring now to FIG. 3, we see the point source of illumination 19, the collimator 13, the object 10 and the detector array 15 with its individual array of optical fibers 15A. FIG. 3 relates the radial direction R to the axial direction which is indicated by the arrow 12 into the plane of the illustration. The curves 10B and 10C, interior of the object 10, illustrate the location of internal details which will be reflected in the image being produced. As shown in FIG. 3, the distance from the source to the tangent point of the beam 14 at the object 10 is the distance A, and the detector array 15 is located a distance B from the same tangent point. In one preferred embodiment of the invention the distance A was several meters, and the distance B was one-half meter. Thus, it should be apparent that FIG. 3 has been distorted for ease of illustration.

FIG. 4 is a view orthogonal to FIG. 3. Because of the difference in view, we now see the optical fibers 15A, in elevation, and in this view we can see the opto-electric transducer 21, and its placement in relation to the optical fibers 15A.

Figure 5:
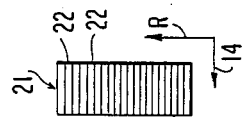
FIG. 5 is a detail of an opto-electric transducer forming a part of the detector array 15.

FIG. 5 shows a plan view of the opto-electric transducer 21. This is seen to comprise an array of detector elements 22, rectangular in form. The elements are adjacent each other and spaced in the direction R. The long dimension of the detector elements lies in the direction of the illumination beam 14, the short dimension is in the radial direction. Typical parameters for the length and width of the detector element are 0.100" and 0.001", providing an aspect ratio of 100.

FIG. 6A is an illustration similar to FIG. 4, with the detector array having been modified for increasing stopping power or detection efficiency. As shown in FIG. 6A, instead of a single detector array 15A, there are three similar detector arrays 15A-15C, arranged in series (or ganged) along the direction of the illumination beam 14. It should be apparent to those skilled in the art that we can combine the electrical signals produced in each of these detector arrays, so as to increase the detection efficiency. We can accomplish this function without degrading resolution in a manner explained in relation to FIG. 6B.

FIG. 6B schematically illustrates a typical ray 14A, emanating from the point source 19. We show typical detector elements 50-52 which can be considered in the detector array 15A, and corresponding detector elements 60-62 which can be considered part of the detector array 15B. Rather than adding signals from corresponding detector elements (adding the signal from element 60 to the signal from element 50, and so on) we project back from detectors 15B (and 15C and so forth) to detector 15A to determine which signals should be added. Thus, since the ray 14A which intercepts detector element 52 also intercepts detector element 61, we add the signals from detector element 61 to the signals from detector element 52, and in this fashion resolution is not degraded although stopping power or detection efficiency is enhanced.

FIG. 6A shows not only detector arrays 15A-15C, but also detector arrays 15X-15Z. The detector arrays 15X-15Z are optional and can be used to decrease imaging time without loss of resolution as will now be explained. The opposed detectors (15X-15Z) are used for decreasing imaging time without loss of resolution. To perform this function the beam width (in the direction 12) is increased beyond that required for our desired axial resolution to such an extent that its width is at least twice what is required. We use one detector array 15A (or a set of detector arrays 15A-15C) to respond to only a portion of the illuminating beam 14, required to provide us with the desired axial resolution. This is accomplished by using the length of the optical fibers to limit resolution, instead of using the beamwidth to determine resolution. We use the opposed detector array 15X (or detector arrays 15X-15Z) to detect energy in a different portion of the beam emanating from the object 10. In this fashion we can illuminate two axial resolution swaths, simultaneously to decrease the examination time without sacrificing resolution.

Figure 7:
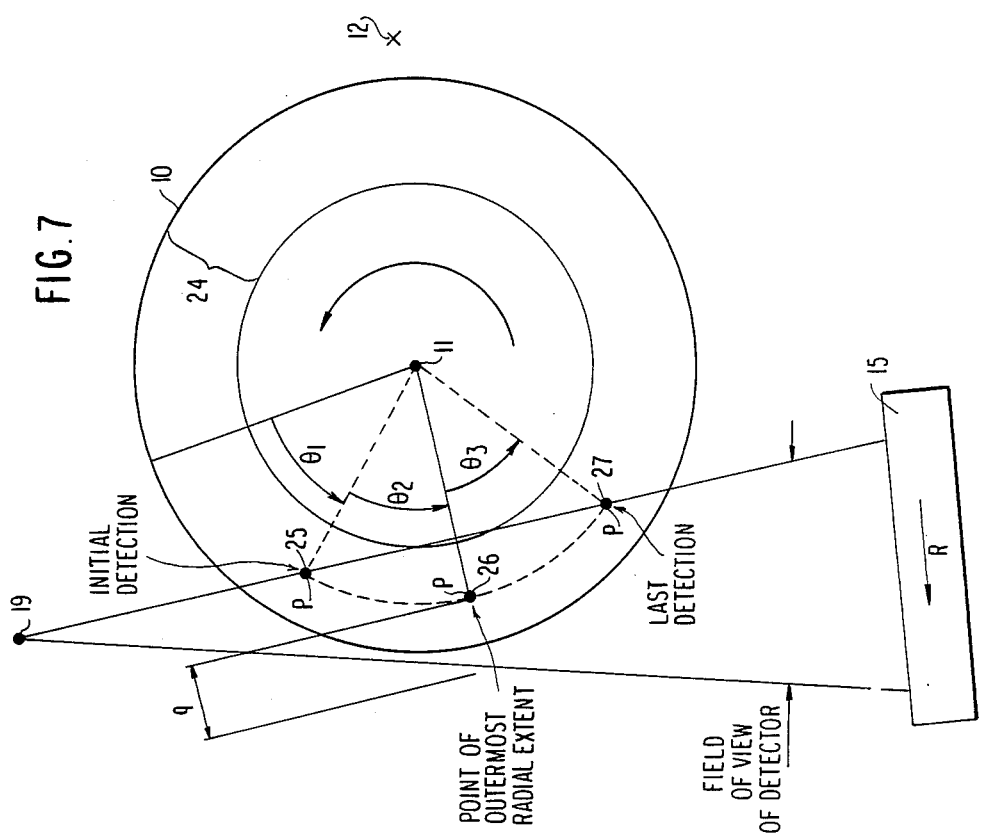

FIG. 7 shows a cross-section of the object 10, the annular region 24 being inspected in relation to the illumination source 19, and the detector array 15. A single anomaly P is illustrated at three different instants of time. At a first instant of time, after the object 10 has been rotated through an angle $\Theta_1$ from some reference position, the anomaly P reaches the position 25 where it first intercepts the illumination beam 14. The presence of the anomaly P produces a response at the detector array 15, the form of that response will be illustrated below. After a passage of some period of time, the anomaly P reaches a position 26, after a further rotation of the object 10 through an angle $\Theta_2$. This is the point of outermost radial extent of the anomaly P into the illumination beam 14. Finally, after the passage of still an additional period of time, the object 10 has rotated through an additional angle of $\Theta_3$ and the anomaly P reaches the position 27. This position is the last position of the anomaly P which will be seen, since it is on the edge of the illumination beam 14.

FIGS. 8-10 show the outputs from the detector array 15 at three different instants in time. We have assumed that the detector array includes detector elements $D_0$ through $D_n$, and at each instant in time each of the detector elements will produce an output representing a scalar indication of the impinging optical photons. FIG. 8 shows the output of the elements at that time at which the object 10 has been rotated through the angle $\Theta_1$ from the reference position. At that instant in time, and assuming that the object 10 is otherwise uniform, the response from each of the detector elements will be identical except for the response from detector element $D_n$, which will indicate the presence of the anomaly P. For this description we have assumed that the anomaly is a point anomaly and therefore affects only a single element, but as will be described below, real defects are not so limited.

Referring now to FIG. 9, the detector response at a later period of time is illustrated, more particularly that period of time at which the anomaly P has reached the position 26. Because of the rotation, the anomaly has moved radially from $D_n$ to $D_{10}$, and thus the uniform response of the detectors is only disturbed at the detector $D_{10}$. Finally, FIG. 10 shows the output of the detectors at still a later point in time, when the anomaly has reached position 27.

Figure 11:
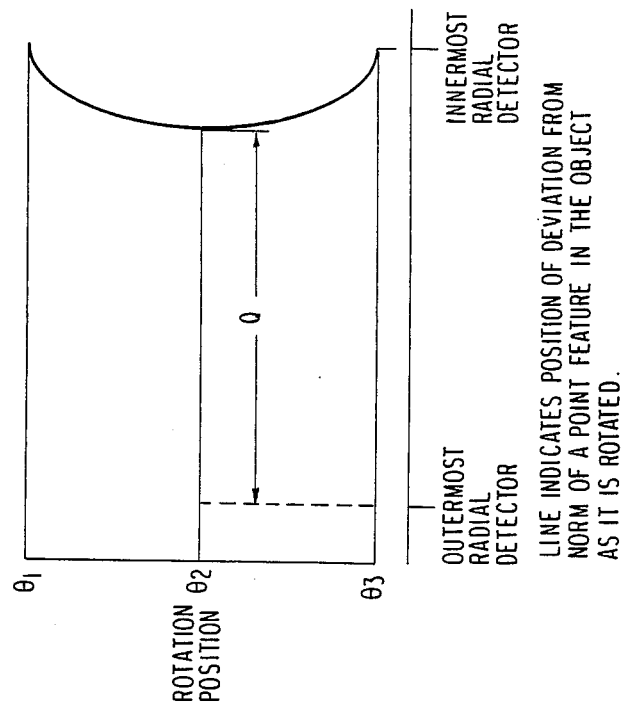

FIG. 11 is the result of plotting the position of the anomaly as a function of rotation. This curve uniquely identifies the location of the anomaly P. The angle $\Theta_1$ at which the anomaly first appears determines the azimuth of the anomaly from the reference line, and thus uniquely identifies a single radial line in the object 10 on which the anomaly appears. The location of the anomaly at angle $\Theta_2$ identifies the point along this radial line at which the anomaly exists. This is identified as the furthest indication of the point P toward the surface of the object 10. The distance Q is directly related to the radial distance q (see FIG. 7) between the anomaly P and the image of the outermost detector $D_0$. Since any real anomaly can be considered a superposition of point anomalies, any real anomaly can be located and measured in this fashion.

Referring back to FIG. 1, it will be appreciated by those skilled in the art that as the object 10 is rotated, the electronics 16 responds to each of the detector elements and stores the resulting signals. Preferably, this operation includes digitization for storage in a digital machine. After the object 10 is rotated substantially 360°, the signals stored in the electronics 16 represent the density or uniformity of the particular annulus of the object 10 which has been illuminated. We can now index the object 10 in the direction 12 relative to the source 18 and detector array 15 to illuminate an adjacent annulus and repeat the location and storage steps. In this fashion, the signals stored in the electronics 16 can be made to represent that portion of the object 10 illuminated.

Using the techniques described in relation to FIGS. 7-11 we can then examine the resulting signals to locate any anomaly in the response, and this analysis can be performed by a suitable machine under appropriate program control.

More particularly, by well known techniques we can synchronize the data storage to the rotational position of the object 10. Thus as an example we could digitize and store the output of the detector 15 for every one degree change in rotational position of the object 10. Each element in the detector array 15 provides us with a scalar quantity indicative of the projected x-ray attenuation of the object 10. Thus for each one degree of angular position we have a number of scalar quantities equal to the number of elements in the detector array. This will be hereinafter referred to as a "line" of data. Since we have assumed taking a "line" of data for each one degree of rotational movement, a single swath will give us 360 "lines" of data. This data can then be plotted (on a CRT or a printer). FIG. 12 shows a matrix representation of that data, wherein each element of the matrix $(W_{x,y})$ is contained in a "line" x, and is derived from a detector element y. A perfectly homogenous swath of the object 10 will produce such a matrix with substantially no variation in the values of the data words. On the other hand, any anomaly or lack of uniformity will be indicated by one or more data words of magnitude greater or less than the others. Rather than plotting the raw data, a relatively simple analysis would be to plot not the raw data, but the difference between the raw data at each point in the matrix and the average. Simple reflection will indicate that an anomaly which has the physical form of a circle about the object's axis of revolution will result in a straight line plot in this matrix. A single point anomaly will also produce a smooth curve in the matrix, the geometry of which depends upon the radial position of the anomaly. Since any real anomaly is made up of a sequence of such "points", such a plot of a real anomaly will be an orderly collection of such smooth curves. Noise or otherwise unwanted data variations can thus be readily identified and eliminated.

Once we have collected the data and loaded it into a matrix such as that shown in FIG. 12, the data can be analyzed either by an operator, or preferably automatically. In order to provide for automatic analysis of the data, we must be able to correlate the indication of a single anomaly through various "lines" of the data so that we can determine its closest approach to one edge of the detector (the parameter q of FIG. 7). This will identify the radial position of the anomaly (as lying a distance q radially downward from the surface), and at the same time, the azimuth (or line) at which the anomaly is first seen can determine the angle, from the reference, of the radial line on which the anomaly lies. So long as we know the relationship between the different "lines" of the matrix and our reference azimuth, we can determine the radial position of the anomaly once we know the line of the matrix on which the anomaly provides the closest approach to the surface; the azimuth of the anomaly is determined from the "line" in which the first anomaly indication is "seen".

Assuming that we can identify the coordinates i,j corresponding to the word $W_{i,j}$, which corresponds to the closest approach of the anomaly to the outermost detector, then from the parameters i,j we can determine the radial distance Q; by following anomaly indications back to the "line" in which it is first seen we determine its azimuth.

However, we must also provide for the possibility that there will be more than a single anomaly in the matrix. In order to determine the information we want, we must be able to track or correlate an anomaly as its indication appear in different "lines" of the data. The anomaly indications should be "connected" by appearing relatively close together in "adjacent" "lines" of the matrix. By determining which anomaly indications are "connected" we can then determine from such a string of connected anomaly indications the one which satisfies our criteria. Such processing is shown in the flow chart of FIGS. 13A and 13B.

Figure 13A:
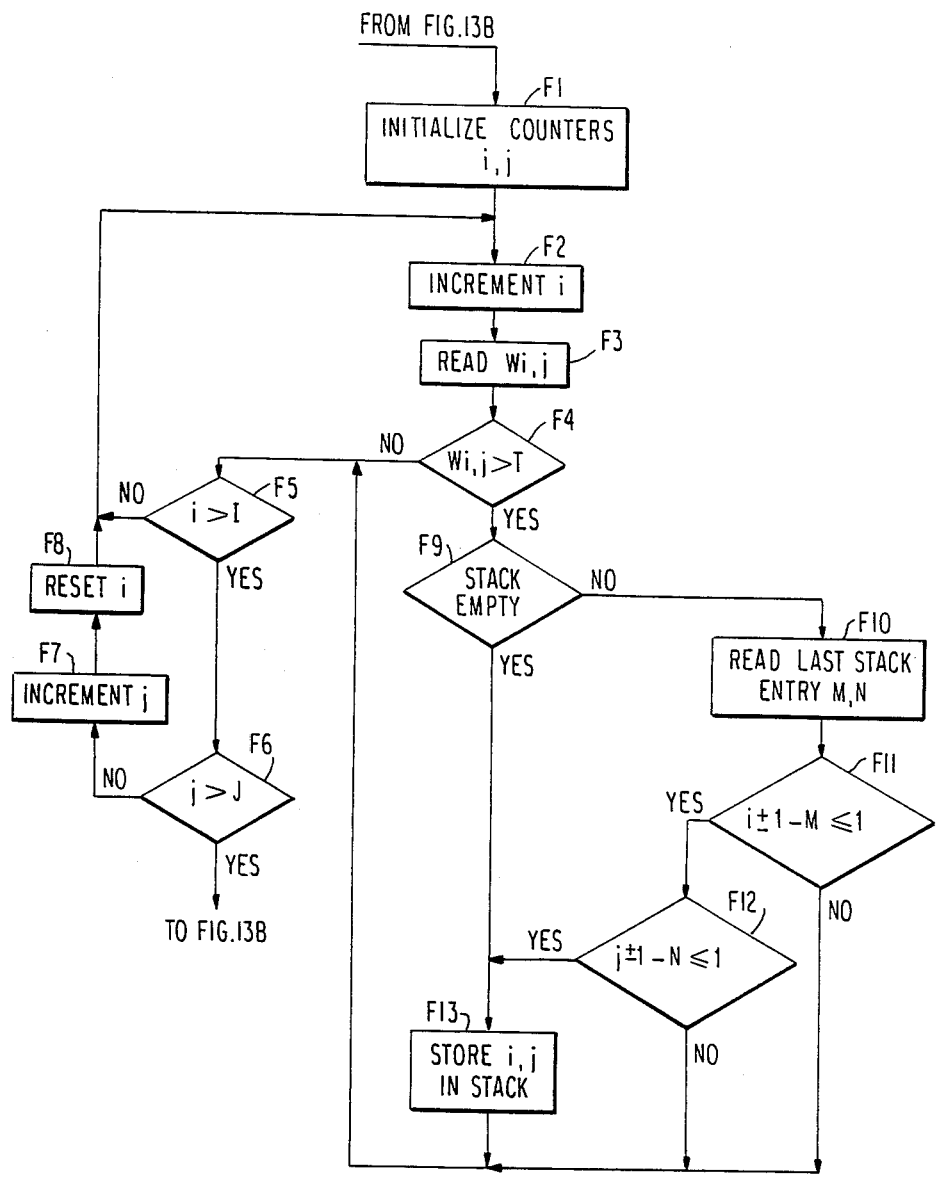
FIGS. 13A and 13B are a flow chart for a suitable program to locate, by machine analysis, anamolies in the collected data.
Figure 13B:
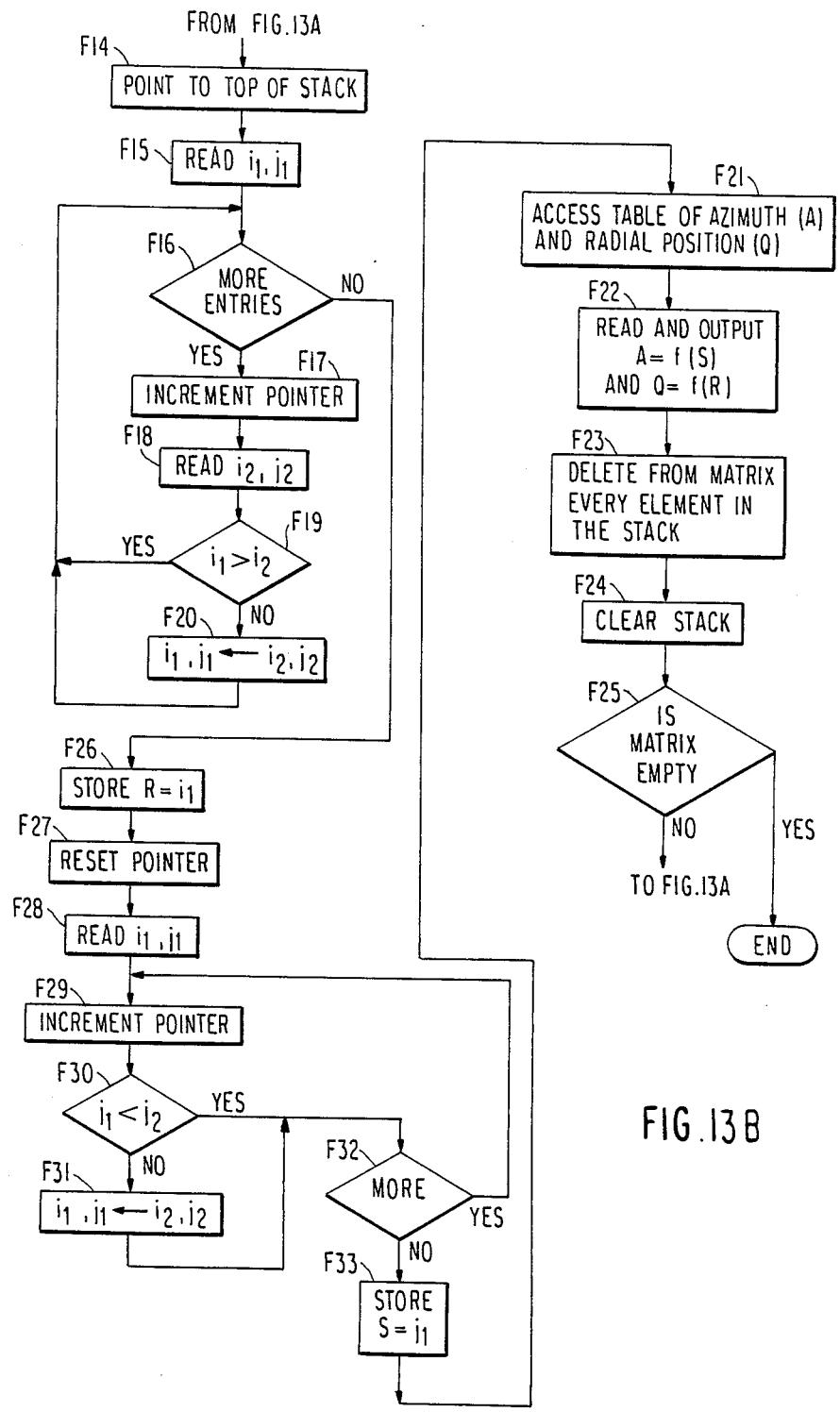

Referring now to FIG. 13A, we employ two counters i and j; function F1 initializes these counters. Function F2 increments one counter i. Function F3 reads the word at the matrix position i,j. Function F4 thresholds this word by determining if it is greater than a predetermined constant T. The constant T can be selected to "filter" out data which is not indicative of anomaly which should be analyzed. Assuming that our candidate word does not pass our thresholding test, then function F5 determines if we have incremented the counter i to the "end" of the matrix represented by the constant I (have we reached the last "column" in the matrix). If not, we loop back and increment the counter i again. Once function F4 identifies a word which passes our thresholding test then function F9 determines if the stack (or memory region) we are going to put these words in is empty. Assuming it is, then function F13 merely stores this word or more particularly, the quantities i,j in our stack and the loop of processing is again entered at function F5. After we have incremented our counter i to the "end", then function F5 will be satisfied and function F6 determines if we have incremented through the matrix in the other dimension to the end represented by the constant J (have we reached the last "row" in the matrix). If we have not, function F7 increments the counter j, function F8 resets the counter i and we loop back again looking for anomaly indications which pass our thresholding test of function F4. The next time we find such a word we will determine (at function F9) that the stack is not empty. Accordingly, rather than merely storing the parameters i,j related to the new word in the stack, function F10 is performed to read the last entry of the stack and to obtain the parameters M,N (corresponding to i,j). Function F11 then tests the parameter i of the current word to see if it is "connected" to our last entry. If it is not, then we ignore the word and go back to continue processing at function F5. We do not want to consider together anomaly indications which are not "connected". Even if our candidate word passes the test of function F11, we impose a further test (of function F12). The candidate anomaly indication must be "connected" in both dimensions before it will be accepted. Assuming that both tests are passed, then the candidate anomaly indication is stored in the stack, along with all previous anomaly indications which have passed our test. The processing continues until we have gone through the matrix and function F6 is satisfied.

At that point we will have, in the stack, the coordinates of all anomaly indications which are "connected". With the stack in this condition we continue processing in FIG. 13B.

Now that we have segregated the anomaly indications from a single anomaly, we need merely (1) identify that indication which satisfies our condition, for closest approach to the outermost detector and (2) that "line" in which the anomaly is first seen. Function F14 points to the top of the stack and function F15 reads the first entry, $i_1$, $j_1$. Function F16 determines if there are any more entries in the stack. Assuming there are, function F17 increments our stack pointer and function F18 reads the next entry corresponding to $i_2$, $j_2$. Function F19 compares $i_1$ to $i_2$. For this processing, we are attempting to locate the anomaly indication with an extreme value of i. (While this extreme value could be "large" or "small" depending on our numbering convention, we assume the "largest" i is what we want. This assumption is merely for convenience.) Therefore if $i_1$ is greater than $i_2$, we are going to retain it and loop back, at function F16 to examine any other entries. On the other hand, if $i_1$ is smaller than $i_2$ then function F20 is performed to transfer $i_2$, $j_2$ to $i_1$, $j_1$, and then loop back looking for more entries. Once we have examined each of the entries in the stack, we have identified as $i_1$, $j_1$ that anomaly indication which makes the closest approach to the outermost detector.

It should be apparent from a review of FIG. 7 that we can predetermine, relative to the dimensions of the actual object, the radial distance of the anomaly below the object's surface to that detector which identifies the anomaly's closest approach to the outermost detector. This table then correlates j to azimuth A and i to radial position Q. Referring again to FIG. 7 it will be apparent that any "line" of data may have contributions from anomalies within a range dependent on the radial position of the anomaly. For the anomaly P it will be "seen" in lines of data from azimuth A in the range $\Theta_1 < A < \Theta_1 + \Theta_2 + \Theta_3$. However, the azimuth of an anomaly can be determined from the azimuth at which the anomaly is first or last "seen"; for anomaly P, $\Theta_1$ or $\Theta_1 + \Theta_2 + \Theta_3$. This can be determined from our stack by determining the largest or smallest parameter j. That is the function of steps F27–F33. First (step F26) we store $i_1$ as R. Steps F27–F33 are similar to F15–F20, but we locate the lowest j, the "line" at which the anomaly indication is first seen. We store this as S (F33). Then function F21 merely uses R and S to access or table to read azimuth and radial location (at F22). Function F23 then deletes from the matrix every element which is stored in our stack thus ensuring that in further processing we look at indications of other different anomalies. Function F24 then clears the stack. The final test of function F25 is performed to determine if there are any indications left in our matrix. If there are, then processing loops back to FIG. 13A to reperform function F1 again. On the other hand, if the matrix is empty we have completed the processing.

For each of a series of "connected" anomaly indications, we will have determined the azimuth and radial position of the anomaly. Thereafter, operator analysis can be restricted to examining the data corresponding to this anomaly in order to determine other parameters of the anomaly such as its size, etc.

Of course to cover the entire object we will need a sequence of such swaths giving us a sequence of such matrices. Correlation of plural matrices will allow identification of anomalies which cut across swath boundaries. Thus anomaly location and size in a swath is determined from the matrix of the swath. Location of an anomaly in size parallel to the revolution axis is determined from the identification of which matrices contain indications of the anomaly.

Although characteristics of certain preferred embodiments have been specifically shown and described, it should be understood that many changes and modifications can be made therein without departing from the spirit and scope of the invention which is to be interpreted from the claims appended hereto. For example, FIG. 1 suggests imaging an annulus of limited radial extent, however, there is no reason why the detector 15 and the beam 14 need be restricted to image anything less than the entire radius of the object.

We claim:

1. A high resolution imaging device where resolution is not degraded by high energy illumination, comprising:
   a source of high energy illuminating radiation directed at an object to be imaged,
   means for supporting said object and for advancing said object in a first direction relative to said source of high energy illuminating radiation,
   detector means for developing electrical signals representative of portions of said object illuminated by said high energy illuminating radiation, said detector means comprising,
   plural scintillating optical fibers each with a longitudinal axis, said plural scintillating optical fibers located to intercept said illuminating radiation with longitudinal axes substantially perpendicular to a path of said illuminating radiation and parallel to said first direction,
   an opto-electric transducer arranged to image one end of said scintillating optical fibers,
   wherein said scintillating optical fibers are arranged in groups and said opto-electric transducer has a plurality of opto-electric transducer elements, each opto-electric transducer element arranged to image one end of different groups of said scintillating optical fibers,
   means for storing a representation of an electrical signal, output from said opto-electric transducer elements, and
   data analysis means responsive to stored signal representations for producing a visual representation of anomalies in said object in a matrix format plotting angular orientation versus radial position.

2. The device of claim 1 which includes at least two opto-electric transducers located on opposite sides of said path of illuminating radiation.

3. The device of claim 1 in which said opto-electric transducer comprises a parallel array of transducer elements, each with an aspect ratio of about 100 or more.

4. The device of claim 1 which further includes:
   means for rotating said object to be imaged about an axis substantially perpendicular to said path of illuminating radiation.

5. A high resolution imaging system where resolution is not degraded by high energy illumination, comprising:
   a source of high energy illuminating radiation directed at an object to be imaged,
   a support for an object to be imaged including means for rotating said object about a rotation axis substantially perpendicular to a path of said illuminating radiation and for providing relative motion between said object and said source substantially along said rotation axis, and
   detector means for developing electrical signals representative of portions of said object illuminated by said high energy illuminating radiation, said detector means comprising:
   a plurality of scintillating optical fibers, each with a longitudinal axis, said plurality of scintillating optical fibers located substantially parallel to one another and located to intercept said illuminating radiation with said longitudinal axes substantially perpendicular to said path of said illuminating radiation and parallel to said rotation axis,
   wherein said plurality of scintillating optical fibers are arranged in groups and which includes plural opto-electric transducers each arranged for imaging an end of said fibers in one of said groups, and
   wherein two of said opto-electric transducers are arranged on opposite sides of said path of illuminating radiation.

6. The system of claim 5 in which two of said opto-electric transducers are arranged serially along said path of illuminating radiation.

7. The system of claim 5 in which said opto-electric transducers are arranged in a parallel array, each transducer with an aspect ratio of about 100 or more.

8. The system of claim 6 in which said opto-electric transducers are arranged in a parallel array, each transducer with an aspect ratio of about 100 or more.

9. The system of claim 5 which further includes:
   means for storing representations of signals produced by said detector means.

10. The system of claim 9 further including:
    data analysis means responsive to stored signal representations for locating anomalies in said object by locating indications of said anomalies in terms of angular orientation and radial position.

11. An imaging system including:
    a source of penetrating radiation emitting radiation generally in a first direction,
    first means for supporting, rotating about a rotational axis, and indexing along said rotational axis, an object to be imaged, said first means located relative to said source so that said penetrating radiation intercepts at least some portion of said object,
    radiation detecting means including a plurality of scintillating optical fibers, each with a longitudinal axis generally parallel to longitudinal axes of others of said plurality of scintillating optical fibers and to said rotational axis, said radiation detecting means located so that radiation transmitted by said object intercepts said scintillating optical fibers, an opto-electric transducer located generally normal to longitudinal axes of said scintillating optical fibers, said transducer including a plurality of opto-electric transducer elements located adjacent one another and spaced in a direction generally perpendicular to said first direction, each opto-electric transducer element imaging ends of different groups of said scintillating optical fibers, at least two of said opto-electric transducer elements arranged serially along a path of said penetrating radiation, and
    storage means responsive to a time sequence of signals produced by said opto-electric transducer elements for storing representations of said signals in a corresponding sequence.

12. The imaging system of claim 11 which further includes:
    data analysis means responsive to said storage means for locating anomalies in said object by locating angular and radial position of indications of said anomalies in the stored representations, and
    display means responsive to said data analysis means for producing a visual representation of said anomalies,
    whereby anomalies in said object are represented in said visual representation by indications whose position in said visual representation are related to the location in the object of the corresponding anomaly.

13. The imaging apparatus of claim 12 in which said visual representation is in a matrix format which has an extent in one dimension corresponding to the time for a complete revolution of said object.

* * * * *